United States Patent
Scherer et al.

(10) Patent No.: US 7,095,010 B2
(45) Date of Patent: Aug. 22, 2006

(54) SILICON ON INSULATOR RESONATOR SENSORS AND MODULATORS AND METHOD OF OPERATING THE SAME

(75) Inventors: Axel Scherer, Laguna Beach, CA (US); Alex Dickinson, Laguna Beach, CA (US)

(73) Assignee: California Institute of Technology, Pasedena, CA (US)

(*) Notice: Subject to any disclaimer, the term of this patent is extended or adjusted under 35 U.S.C. 154(b) by 249 days.

(21) Appl. No.: 10/729,242

(22) Filed: Dec. 4, 2003

(65) Prior Publication Data

US 2004/0146431 A1    Jul. 29, 2004

Related U.S. Application Data

(60) Provisional application No. 60/430,846, filed on Dec. 4, 2002.

(51) Int. Cl.
*G01J 1/04*    (2006.01)
*G02B 6/00*    (2006.01)

(52) U.S. Cl. .................. 250/227.11; 385/12; 385/30

(58) Field of Classification Search .......... 250/227.11; 385/12, 30
See application file for complete search history.

(56) References Cited

U.S. PATENT DOCUMENTS 5,846,708 A * 12/1998 Hollis et al. .................. 435/6
6,195,187 B1 * 2/2001 Soref et al. .................... 398/9
6,657,731 B1 * 12/2003 Tapalian et al. ............ 356/480
6,661,938 B1 * 12/2003 Lim et al. ..................... 385/12
6,721,053 B1 * 4/2004 Maseeh ...................... 356/436
6,798,947 B1 * 9/2004 Iltchenko ..................... 385/31
2004/0023396 A1 * 2/2004 Boyd et al. ................. 435/872

* cited by examiner

*Primary Examiner*—Thanh X. Luu
(74) *Attorney, Agent, or Firm*—Daniel L. Dawes; Myers Dawes Andras & Sherman

(57) ABSTRACT

A microsensor for sensing a substance comprises a substrate, a source of light, an optical microresonator or semiconductor optical ring microresonator fabricated in the substrate exposed to the substance to allow an interaction between the microresonator and substance, a waveguide coupling the source of light to the optical microresonator, and a detector coupled to the microresonator to measure the resonant frequency of the microresonator, the absorption loss of whispering gallery modes in the microresonator or the quality factor of the microresonator, which are sensitive to interaction of the substance with the optical microresonator. A polymer coating disposed on the microresonator is reactive with the substance. The microsensor may comprise a plurality of microresonators corresponding to a plurality of different resonant frequencies to generate an absorption spectrum of the substance.

11 Claims, 7 Drawing Sheets

SILICON ON INSULATOR RESONATOR SENSORS AND MODULATORS AND METHOD OF OPERATING THE SAME

RELATED APPLICATIONS

The present application is related to U.S. Provisional Patent Application Ser. No. 60/430,846, filed on Dec. 4, 2002, which is incorporated herein by reference and to which priority is claimed pursuant to 35 USC 119.

BACKGROUND OF THE INVENTION

1. Field of the Invention

The invention is related to the field of integration between semiconductor optical circuits and electrical circuits, and in particular as utilized as chemical or biosensors.

2. Description of the Prior Art

It has recently become possible to define optical filters and fiber optic mode couplers with excellent performance in silicon on insulator (SOI) chips. The combination of low fiber-coupling insertion losses, low waveguide losses and high refractive index contrast enables the miniaturization of high quality optical elements in silicon waveguides surrounded by $SiO_2$. By leveraging the fabrication quality provided by silicon microelectronics foundries, high resolution optical elements can now be fabricated with excellent reproducibility and uniformity on 8" wafers.

BRIEF SUMMARY OF THE INVENTION

The rapid identification of air-borne and fluidic chemicals without the need for elaborate laboratory facilities has long been an important aim of miniaturization. This ability has become even more crucial in biology and medicine, where the rapid analysis of pathogens, DNA fingerprinting of bacteria and human ailments, and multiple disease detection requires increasingly complex measurement systems. Other areas of interest which benefit from small and accurate ambient detectors include toxic gas sensors for a large variety of safety applications. Even specialized all-optical read-out applications of flammable gases, in which the insertion of electronics is not desirable, can easily be satisfied by the sensor approach of the invention by coupling the filtered light from the resonator filters to a read-out fiber through a grating coupler. Such a silicon CMOS-based read-out chip, manufacturable in very large quantities by standard SOI microchip technology, can be modified to match the desired application through the deposition of appropriate organic polymers onto large arrays of ultrasmall optical resonant cavities. The improvements in sensitivity and size, together with the cost savings resulting from integrating both sensing optics and read-out electronics on the same substrate, result in many applications of the test-chips for chemical and biological sensing. Moreover, the electronic chip design and optical filters form a common generic platform that can be functionalized for many different analyses. The unprecedented capability for massive integration of optical sensor elements and read-out electronics on the same platform may eventually permit the parallel monitoring of millions of reactions.

Spectroscopy of chemical and biological samples on a silicon detection chip holds an enormous potential for the rapid and inexpensive analysis of small amounts of material. The illustrated embodiment is a new micro-resonator based analysis system, which relies on well-established silicon technology, and which can detect very small quantities of reagent. These detector systems not only detect air-borne agents, but are also integrated with microfluidic systems that deliver picoliter control over reagent quantities.

The illustrated embodiment is comprised of high finesse optical cavities, fabricated in silicon, to analyze samples by measuring chemical or bio-induced optical changes in tens of thousands of different functionalizing materials. Changes in the coupling of light from silicon waveguides into microresonators are detected with germanium detectors, and multi-element optical detector systems are provided. Ring resonators are coated with surface layers that bond to specific reagents, and the de-tuning of frequency or absorption losses of the narrow spectrum whispering gallery modes will be measured with germanium detectors. By identifying resonators with changing parameters, and by using the resonator quality to multiply the effective interaction path length of light with the sensing polymer, it is possible to detect ambient chemicals with very high sensitivity.

The invention is a nanophotonic chip fabricated in a complementary metal oxide semiconductor (CMOS) fabrication line which has been functionalized to perform chemical sensing. The chip includes compact, inexpensive and sensitive chemical sensor arrays, constructed by standard silicon foundry processing. The sensors are optically interrogated by near-infrared light in the 1550 nm C-band and 1320 nm O-band telecommunications wavelength ranges, which ensures compatibility with commercially available optical sources, amplifiers and detectors. At these wavelengths, single crystal silicon as found in SOI active layers is almost perfectly transparent and lends itself to the efficient guiding of light. The devices offer robust chemical analysis with no moving parts and high sensitivity. Redundancy and scaling of the number of sensor elements is provided by the very small sensor sizes and the selective functionalization of individual optical devices, as well as integrated on-chip electronic interrogation which can add intelligence to the chemical analysis task.

More specifically, the invention is a microsensor for sensing a substance comprising a substrate, a source of light, an optical microresonator fabricated in the substrate exposed to the substance to allow an interaction between the microresonator and substance, a waveguide coupling the source of light to the optical microresonator, and a detector coupled to the microresonator to measure a performance parameter of the optical microresonator sensitive to interaction of the substance with the optical microresonator.

The microsensor further comprises a polymer coating disposed on the microresonator, which polymer coating is reactive with the substance.

In the illustrated embodiment the microsensor is a semiconductor optical ring resonator, typically with a Q of 10,000 or greater. The detected performance parameter is the resonant frequency of the resonator. For example, the performance parameter is the absorption loss of whispering gallery modes in the resonator or the quality factor of the resonator.

In the illustrated embodiment the detector is a germanium detector and the substrate is a silicon-on-insulator (SOI) heterostructure.

The microsensor further comprises CMOS integrated read-out circuitry fabricated in the same substrate and coupled to the germanium detector. The detector comprises a read-out optic fiber coupled to a grating coupler.

Even more generally the microsensor comprises a plurality of microresonators and a corresponding plurality of detectors formed into an array coupled by the waveguide to the light source in which the plurality of microresonators are exposed to a plurality of substances. In this embodiment the microsensor further comprises an addressing circuit for reading the array, namely CMOS integrated read-out circuitry fabricated in the substrate coupled to the addressing circuit. In one embodiment the detector comprises a polycrystalline germanium detector fabricated proximate to the microresonator.

In the illustrated embodiment the detector is deposited onto the waveguide during a post-processing step following CMOS fabrication of the waveguide.

The microsensor may further comprise a microfluidic circuit for communicating the substance to the microresonator. In this embodiment the microfluidic circuit comprises pneumatic valves and peristaltic pumps defined by multi-layer replication lithography for delivering picoliter volumes of the substance to the microresonator.

The microresonator is characterized by an optical absorption loss determined by direct optical excitation of the substance when in contact with the microresonator.

In general the microsensor may comprise a plurality of microresonators corresponding to a plurality of different resonant frequencies to generate an absorption spectrum of the substance.

In one embodiment the coating on the microsensor reacts with the substance to form an altered optical parameter which in turn alters an optical parameter of the microresonator. The altered optical parameter is the refractive index of the coating or the waveguide loss of the microresonator. In another embodiment the coating is reacts specifically with the substance. In still another embodiment the coating reacts specifically with the substance by means of an enzyme linked immunosorbent assay (ELISA).

The invention also includes methods for making and using the above microsensors as described.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 12b is an enlargement of one of the sensor cells used in the array of FIG. 12a.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
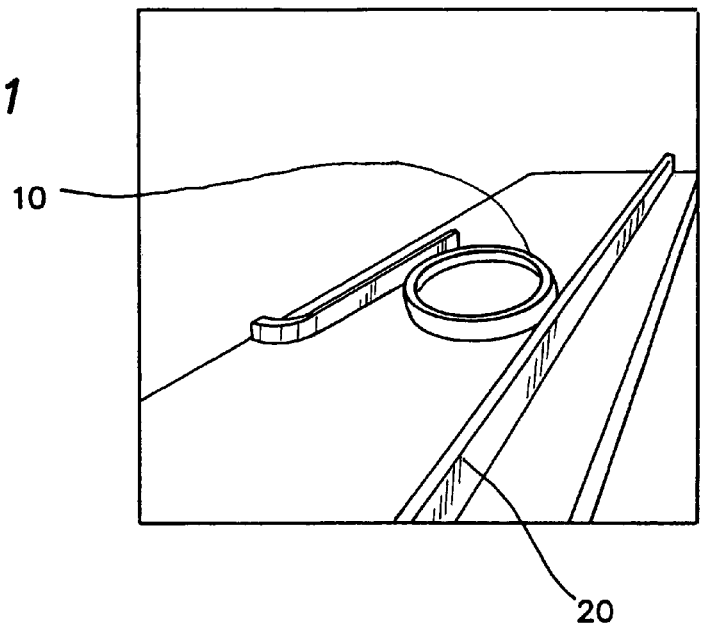
FIG. 1 is a microphotograph of the bio-chemical sensor or resonator of the invention which is based on chemically activated absorption or refractive index change at the micro-disk and micro-ring surfaces of resonator.

The illustrated embodiment is a new biochemical sensor or resonator 10 based on chemically activated absorption or refractive index change at the micro-disk and micro-ring surfaces of resonator 10, a microphotograph of which is shown in FIG. 1. When individual resonators 10 are coated with different organic reagents, a chemically selective sensor can be built. Only those resonators 10 made or coated with a reacting organic reagent will change with time during the measurement, and specific chemicals can be accurately identified by analyzing many (thousands to millions) of resonators 10 provided in a large scale chip or array 12 shown in FIG. 12a, which is described below. The information from these resonators 10 is expected to require massive analysis, which is only possible by using complex CMOS electronics 14, which is fabricated in parallel with the optical sensor elements or resonators 10 during the fabrication of the analysis chips 12.

Figure 3:
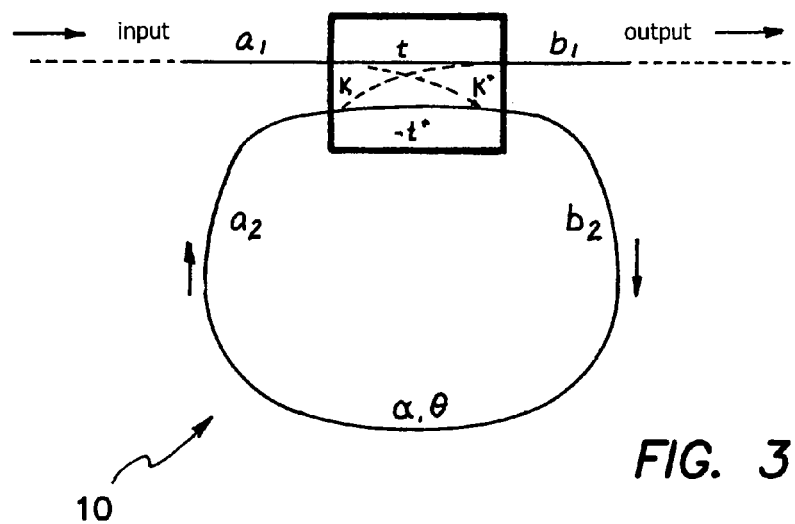
FIG. 3 is a schematic illustration of an optical resonator ring.

The basic element used in the sensors 22 of the illustrated embodiment is a ring resonator 10 as schematically shown in FIG. 3. Quality factors in excess of 20,000 have been demonstrated for micro-ring resonator 10 when defined in silicon by CMOS processing. For the sensor application, such rings 10 are coated with thin polymer layers 16 shown in FIG. 12b, which are chosen to react with high specificity with chemical agents in their ambient surrounding resulting in change of the refractive index or absorption. The change in optical properties in turn results in a change in the effective refractive index or path length of the ring resonator 10, which can be optically measured as a change in the resonance frequency or quality factor. Refractive index changes as low as 0.01% can be monitored by polycrystalline germanium detectors 18 fabricated next to every resonator 10. Detectors 18 are deposited onto the drop waveguides 20 of the resonators 10 during a post-processing step following CMOS fabrication of the waveguides 20 and the measurement electronics 14. FIG. 12b is a block diagram of the electronics 14 for each sensor 22 in array 12 in FIG. 12a. Electronics 14 is comprised of an analog-to-digital converter 24 coupled to detector 18, which converter 24 has its output coupled to an N bit SRAM 26. SRAM 26 in turn is coupled to a conventional word line 28 and a N bit bitline 30. A plurality of sensors 22 are combined in the array 12 of FIG. 12a and addressed through a conventional CMOS column decoder and multiplexer 32 coupled to conventional CMOS N bit sense amplifiers 34 coupled to bit lines 30 and through a conventional CMOS row decoder 36 coupled to word lines 28.

A plurality of resonators 10, when coated with a plurality of different functionalizing polymers 16, are then used in sensor array 12 for the rapid parallel analysis and identification of a plurality of unknown chemicals. Moreover, standard CMOS electronics 14 is used to amplify signals read from several detectors 18, and to perform required thresholding and analysis functions, which intelligently evaluate the light intensity information gathered by the resonator filtered detector array 12. The ring resonators are inherently filtering as described below.

Figure 12A:
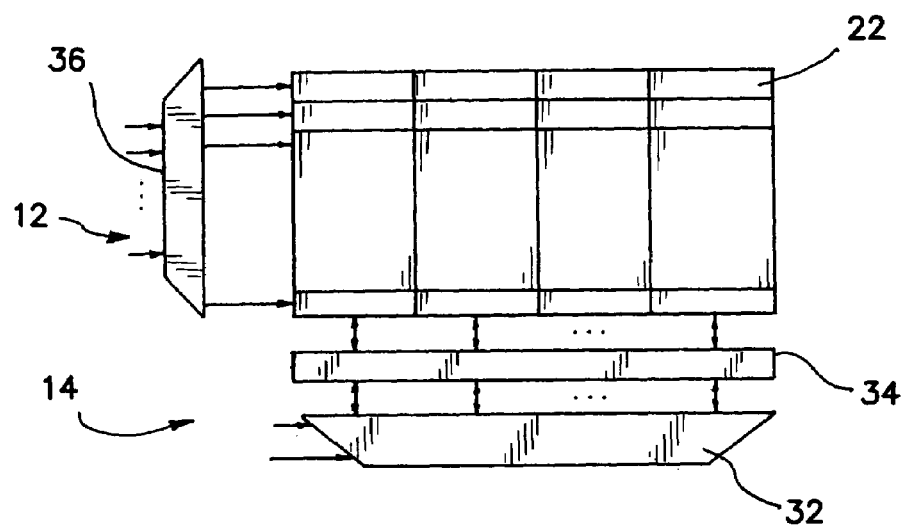
FIG. 12a is a simplified block diagram of a RAM array of the sensors of the invention.
Figure 12B:
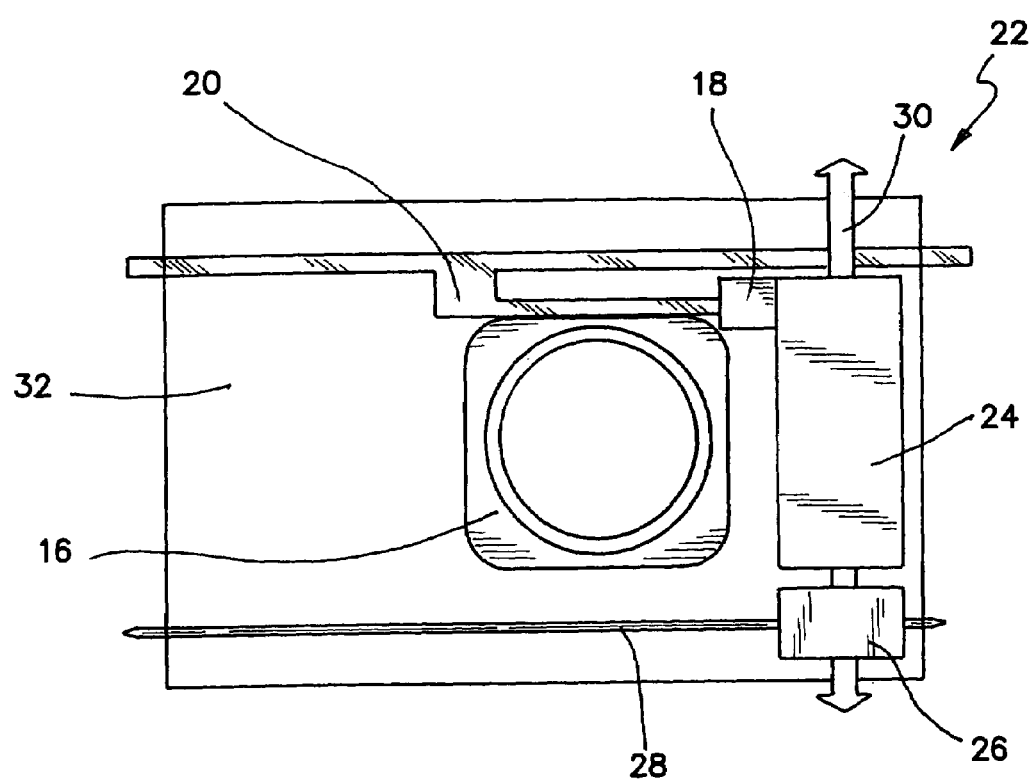
FIG. 12b is

Additionally, manufacture by means of CMOS functionality permits the construction of very large arrays 12 of sensors 22 (e.g. 100,000 to 1,000,000 sensors) by leveraging RAM-type structures for addressing as shown in FIGS. 12a and 12b. Chip-based optical sensor development converts SOI nanophotonic chips into compact monolithic multi-element sensors arrays 12 with integrated electronics 14 for rapid data analysis.

Optical Disk and Ring Resonators

Micro-lithography also enables the definition of large numbers of small high-Q disk and ring resonators 10 with high quality factors of above 10,000. These high Q values translate into long interaction lengths between light and the material surrounding the resonator cavities or resonators 10. These resonators 10 are used as optical add/drop filters when defined or fabricated in proximity to microfabricated waveguides 20. When the losses in the resonator 10 match the coupling strength between the waveguide 14 and the resonator 10, it is possible to efficiently filter out specific frequencies of light whose wavelengths match the whispering gallery modes supported by the microresonators 10 as diagrammed in FIG. 3.

It is possible to control the efficiency of filtering into these resonators 10 from the input waveguides 20 by either (a) changing the optical index of refraction between the resonator 10 and the waveguide 20 or by (b) changing the losses in the resonator 10. When the losses in the resonators 10 exactly match the coupling strength between the waveguides 20 and the resonators 10, critical coupling is achieved and all of the power at the resonant wavelength is diverted from the input waveguide 20 into the resonator 10. Any change in the geometry of these resonators 10, including a change in the refractive index at their surface, results in a measurable change of either the losses or the path length of the resonator 10.

In the illustrated embodiment the surface of resonators 10 are chemically functionalized, fabricated by conventional silicon fabrication on silicon-on-insulator (SOI) wafers 32 indicated in FIG. 12b, as optical sensors 22 for chemical reactions. To functionalize these resonators 10, they are coated with selective reagents, which only react with specific chemical or biological compounds in the ambient surrounding the resonators 10 by using microfluidic templating methods. Microfluidic templating is a process by which elastomeric fluid channels are aligned on top of the sensor chip and solutions are pumped through the fluid channels leaving residue on the chip surface. After coating the elastomeric fluid channels is peeled off and the residue remains.

Figure 2:
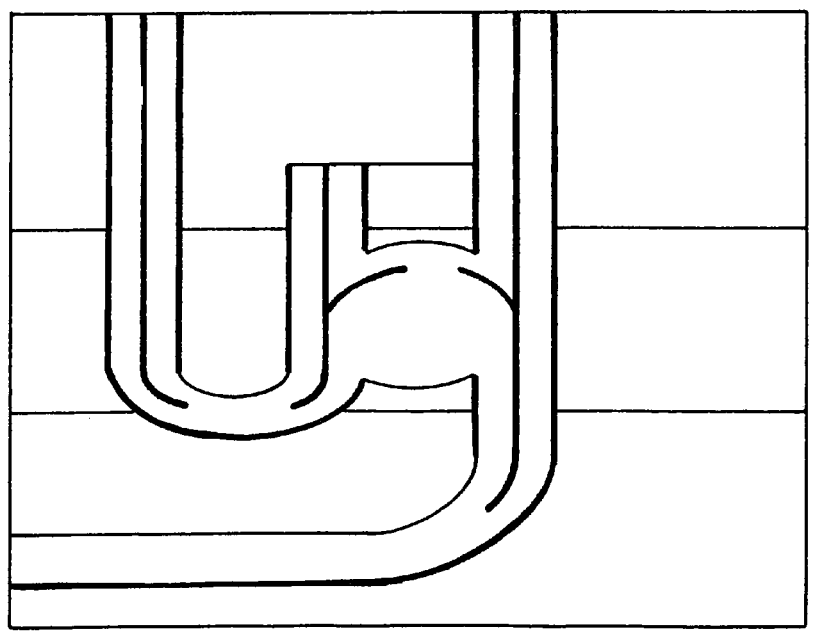
FIG. 2 is shows a portion of a fluidic system wherein picoliter volumes of reagents are sorted, concentrated, and delivered to the detector surfaces by using pneumatic valves and peristaltic pumps defined by multi-layer replication lithography.

These compact bio-functionalized optical sensor arrays 12 are used as detectors to determine the composition of airborne gases and fluidic samples flowing through replication molded elastomeric flow channels. Picoliter volumes of reagents are sorted, concentrated, and delivered to detector surfaces by using pneumatic valves and peristaltic pumps defined by multi-layer replication lithography as illustrated in FIG. 2. See U.S. patent applications Chou et.al., Ser. No. 09/724,784, filed on Nov. 28, 2000 entitled, "Microfabricated Elastomeric Valve and Pump System"; Unger et.al., Ser. No. 09/826,583, filed on Apr. 6, 2001 entitled "Microfabricated Elastomeric Valve and Pump Systems," Quake et.al., Ser. No. 09/997,205 filed on Nov. 28, 2001, entitled, "Microfabricated Elastomeric Valve and Pump Systems,"; Chou et.al., Ser. No. 09/724,967, filed on Nov. 28, 2000, entitled "Microfabricated Elastomeric Valve and Pump System,"; Chou et.al., Ser. No. 09/796,378, filed on Feb. 28, 2001, entitled "Microfabricated Elastomeric Valve and Pump Systems"; Chou et.al., Ser. No. 09/796,871 filed on Feb. 28, 2001 entitled "Microfabricated Elastomeric Valve and Pump Systems;" Chou et.al., "Microfabricated Elastomeric Valve and Pump Systems," U.S. Pat. No. 6,408,878 (2002); Chou et.al., Ser. No. 10/150,895 filed on May 15, 2002 entitled "Microfabricated Elastomeric Valve and Pump Systems"; Unger et.al., Ser. No. 09/605,520 filed on Jun. 27, 2000 entitled "Microfabricated Elastomeric Valve and Pump Systems', all of which are incorporated herein by reference. Mature electronic microfabrication techniques along with our recent advances in microfluidic techniques to manipulate small volumes of reagents are combined to result in a sensitive analysis of the composition of biological and chemical agents.

Direct Absorption Measurement

One method for using an optical resonator array 12 for sensing chemicals comprises the step of performing absorption spectroscopy. Light within the resonator 10 is used to excite bonds in the organic material or layer 16 surrounding the resonator ring 10. Thus, absorption losses can be measured at frequencies which match the bond excitation energies. If an array 12 of resonators 10 with slightly different resonance frequencies are constructed, an absorption spectrum can be obtained by observing the losses in the individual resonators 10, each of which are tuned for a different frequency. For this approach, it is desirable to test for materials with unique absorption spectra in the near-infrared measurement wavelength range of 1100–1600 nm. The schemes can be used either for direct spectroscopy or to measure absorption of antibody-linked fluorescent molecules used as markers.

The large Q's of microresonators 10 lead to a tremendous optical path length in a small volume. For example, a Q of 10,000 for a 10 micron diameter microresonator 10 leads to an effective path length of several centimeters, longer than many typical fiber optic sensors. By matching the measured absorption spectra to a library of absorption peaks in common polymers, the accurate composition of the material surrounding the resonators 10 can be identified. Unfortunately, the optical transmission window for silicon waveguides 20 with germanium detectors 18 at 1100–1600 nm is relatively uninteresting for many common organic fluorescent dyes. However, for molecules with absorption peaks within the near infrared range, it is possible to use the optical resonator 10 in a method for determining that absorption through a simple transmission. Many resonators with slightly different dimensions can be used as transmission filters that only transmit particular wavelengths. By reading the amount of transmitted light from each of these filters, an absorption spectrum can be constructed.

Indirect Spectral Measurements.

Figure 4:
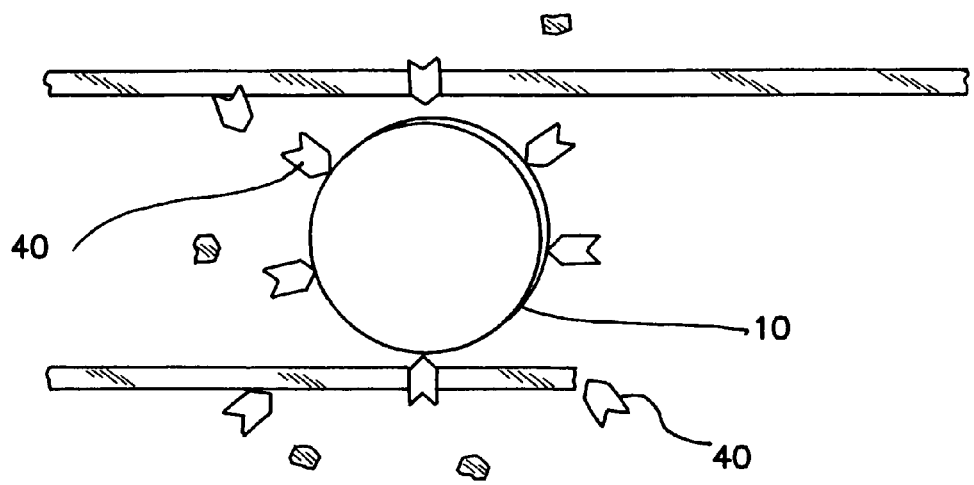
FIG. 4 is a diagram depicting reagents selectively reacting with a coated or functionalized resonator ring or disk.

An alternative method for sensing chemicals is to measure the accumulation of these materials on the specially pretreated surfaces of test resonators 10. These resonators 10 operate at a wavelength unrelated to the bonding energies or vibrational modes of the organic material to be analyzed. Instead, in such indirect measurements, we rely on measuring the change in refractive index and waveguide losses of an optical resonator 10 when polymers 40 attach to the resonator surface as diagrammatically illustrated in the graph of FIG. 4.

This measurement of path length difference is quite generic and can be used for a wide variety of materials. In order to conduct a measurement to determine the change in path length of the resonator 10, it is necessary to coat the resonators 10 with very thin layers of reagents 16 to convert the resonators 10 into optical devices whose optical properties are influenced when specific reagents or analytes attach to their surface. The selectivity of the measurement relies on the selectivity of the surface treatments, which are designed to specifically bond to the desired analytes. The high Q and small size of silicon-based microresonators 10, together with the maturity of silicon CMOS processing facilities and the integration of germanium detectors 18, provide a very sensitive and manufacturable analysis platform for such indirect chemical detectors.

Chemical Biofunctionalization

In a first example of the illustrated embodiment the sensitivity of such a system by direct detection of fluorescent molecules in solution is evaluated. The whispering gallery modes of a micro-resonator 10 immersed in solution are excited using a diode laser (not shown). Laser light is coupled through on optic fiber into a semiconductor grating fabricated on the chip into a chip waveguide and thence to the ring resonator. Detection is made with an on-chip Ge detector and waveguide coupling to the ring resonator as described above. Measurement of the sensitivity of the optical absorption losses to various concentrations of the fluorophores Cy5 (Abs 1100 nm) and Cy5.5 (Abs 1250 nm) are made. Once the parameters of the system have been determined, a "sandwich" immuno-assay is implemented by adopting a commercially available enzyme linked immunosorbent assay (ELISA) kit. A number of protocols have been developed to derivatize a glass surface for bio-molecule attachment, which protocols are modified to work with the silicon micro-rings 10. A "sandwich" immuno-assay is a conventional assay in which the reactive layer is coated with a fluorescent layer and the reaction of interest is detected through a secondary relationship with the fluorescent layer. See also U.S. patent application Unger et.al. Ser. No. 10/416,418 filed on Nov. 16, 2001 entitled "Apparatus and Methods for Conducting High Throughput Screening Assays". Once an assay has been demonstrated with a practice analyte such as ovalbumin, virtually any analyte-antibody sandwich system can be used with the device, including systems important for biological and chemical weapons detection such as ricin, *Staphylococcal enterotoxin B, Francisella tularensis* and *Bacillus globigii*.

If each resonator 10 is coated with a different sensor material 16, and one of these reacts with a reagent. When the reagent is present, only that resonator 10 will change in its properties, and the intensity of the light dropped by that resonator 10 from the waveguide 20 is decreased. This occurs since the resonance frequency and/or the resonance losses will be changed when the chemical surface layer reacts with a chemical that changes its refractive index. We have developed the surface treatment approaches to selectively coat resonators 10 by using elastomeric flow channels.

Deposition of Organic Materials

To functionalize the resonator arrays 18, microfountain pens 42 are used, which we have recently developed. These pens 42 can define 10 micron diameter areas of polymers for the definition of biological assay chips 12. The pens 42 are then robotically manipulated according to conventional machine control to apply the polymer to the selected resonator 10 in array 12. See U.S. patent application Quake et.al. Ser. No. 10/288,248 filed on Nov. 4, 2002, entitled "Microfabricated Fountain Pen Apparatus and Method for Ultra High Density Biological Arrays," which is incorporated herein by reference.

An alternative method for functionalization involves flowing surface functionalization treatments through the elastomeric flow channels over the resonator surfaces. New flow channels are optically aligned to the resonator arrays 12 so that only specific resonators 10 are below the channels through which the chemical surface treatment is pumped. Although selective reagents have also been deposited by stamping, photo-assisted chemical deposition or lithographic deposition through masks in the past, fountain pens 42 provide the best flexibility for deposition of large numbers of different functionalizing polymers.

Figure 5A:
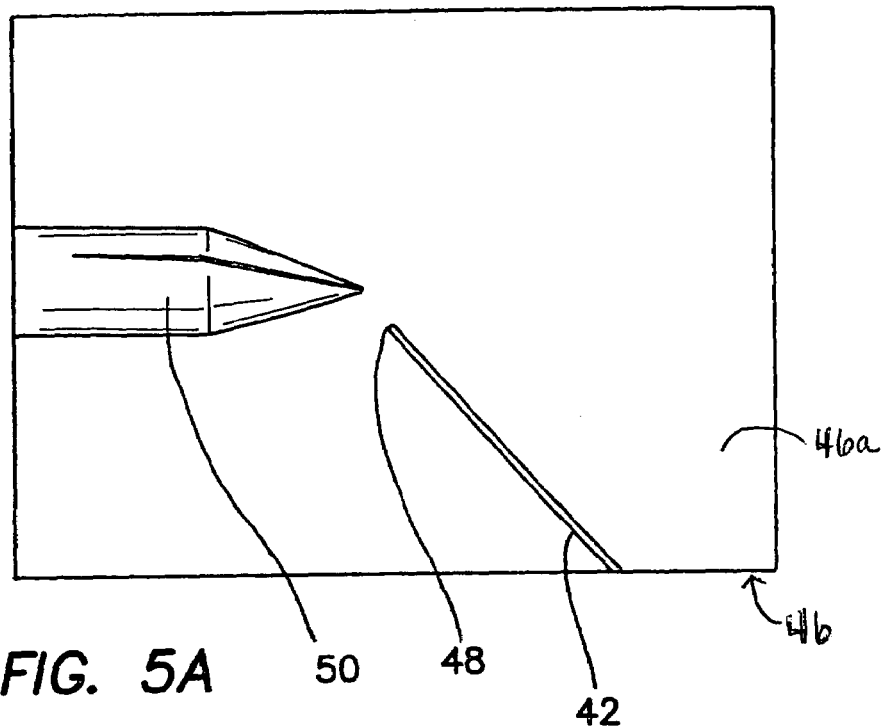
FIG. 5a is a microphotograph showing the pens of the invention used to functionalize an array of rings in comparison to a larger conventional dip pen used to functionalize silicon dioxide slides.
Figure 5B:
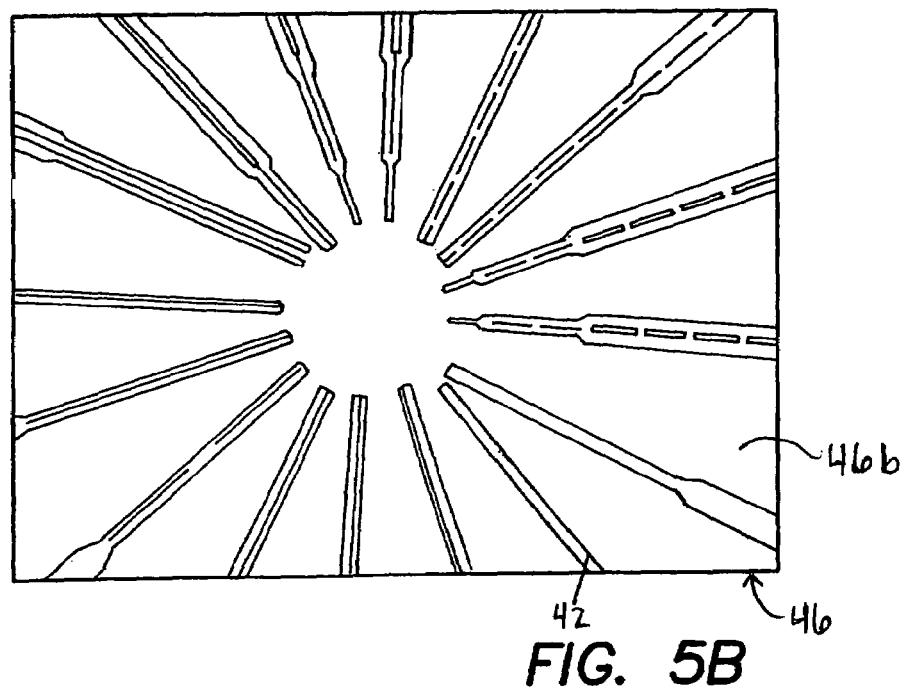
FIG. 5b is a microphotograph showing a plurality of pens of the invention with different profiles.
Figure 6:
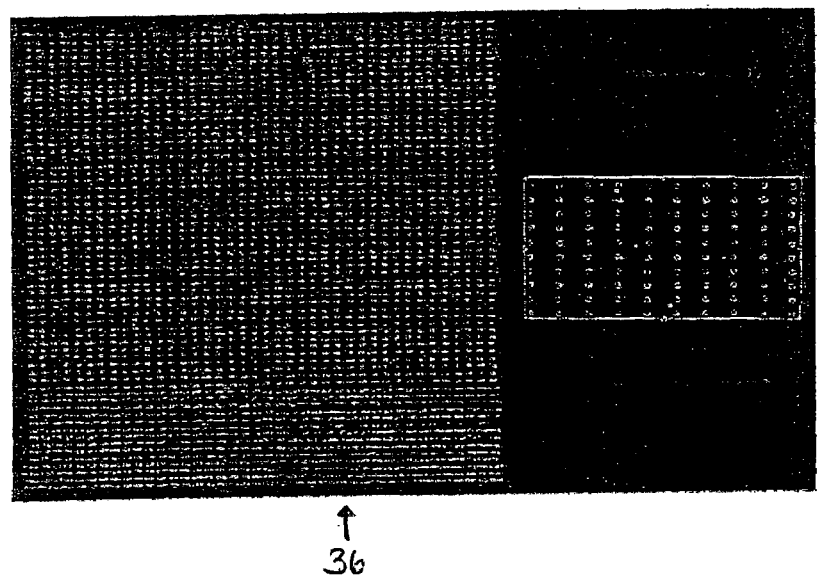
FIG. 6 is a microphotograph demonstrating the resolution of the fountain pen of the invention, where an array 36 of 2500 Xylene cyanol spots were deposited onto a 3.2 mm square region of a glass slide, resulting in a density of 25,000 spots/cm$^2$
Figure 7:
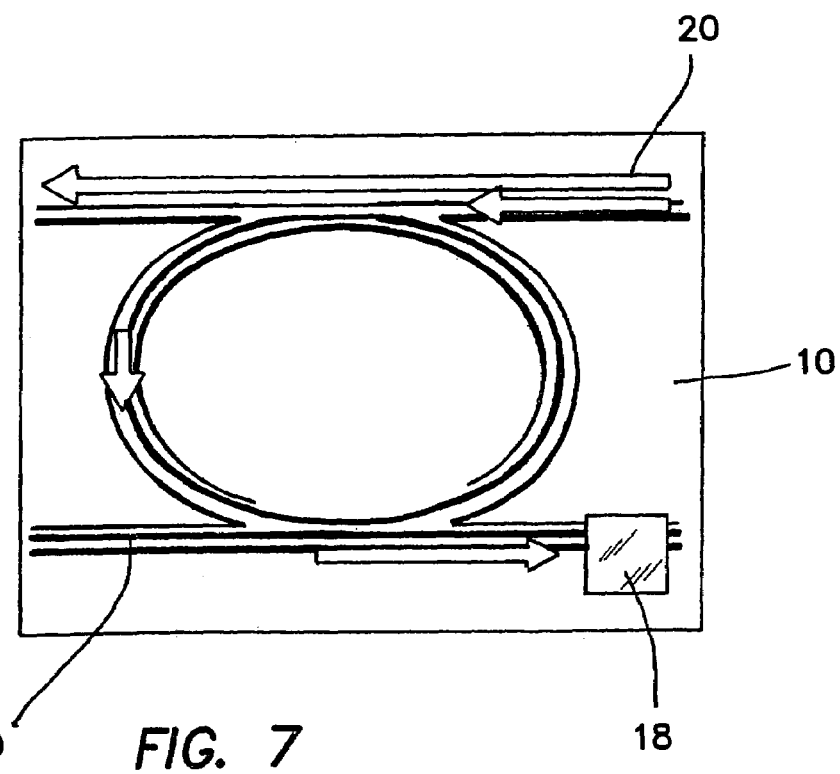
FIG. 7 is a microphotograph showing the connections between an input waveguide, a ring resonator and a germanium detector 18 deposited onto a drop waveguide.

Micrometer-sized fountain pens 42 are fabricated using a two-exposure procedure, etching photolithographic patterns into 12.7 micron thick stainless steel shim stock sheets 46, incorporated herein by reference. Here, such chemically and electrochemically etched fountain pens 42 are used to deposit thin layers of organic materials onto optical resonators 10. During the lithographic exposure of such pens 42, the metal sheet 46 is patterned from both the front 46a and the back surface 46b, and subsequently wet etched from both sides to assume a desire profile, examples of which are shown in the microphotograph of FIG. 5b. By performing lithography on both sides of the stainless steel shim stock 46, it is possible to etch through the 12.7 micron thick steel layer 46 in a single chemical etch, and it is also possible to define slightly different features on the front 46a and back 46b of the shim stock sample 46. To define the pens 42, photoresist masked stainless steel shim stock 46 was subsequently immersed into a mixture of 40 vol % HCl:40 vol % $H_2O$:20 vol % $HNO_3$, which removed the unmasked areas of stainless steel. Low power ultrasonic cleaning was then used to completely remove the photoresist mask layer, the pens 42 were dipped into a thinned polyurethane solution (1 part Ebecryl CL 1039 Acrylated Urethaone: 1 part EtOH: 1% Irgacure 500), and then inverted and exposed in a UV curing oven for 10 minutes. At this point, the pens 42 were ready for use. FIG. 5a is an enlarged photograph showing the distal tip 48 of a typical example of stainless steel fountain pen 42, and provides a comparison with more conventional dip-pens 50 presently used by biologists to define functionalized silicon dioxide slides. The resolution of the fountain pen technology of the invention is clearly demonstrated in FIG. 6, where an array 36 of 2500 Xylene cyanol spots were deposited onto a 3.2 mm square region of a glass slide, resulting in a density of 25,000 spots/cm$^2$ Results a. Optical Interrogation One convenient method used for reading the status of the surface chemistry of the resonator 10 is based on monitoring the intensity of an infrared light signal guided through the waveguide 20 and the resonator 10. In this case, the intensity of light dropped from the input waveguide 20 through the insertion of a ring resonator 10 is determined with a germanium detector 18 deposited onto the drop waveguide 20', as shown in FIG. 7.

Figure 8:
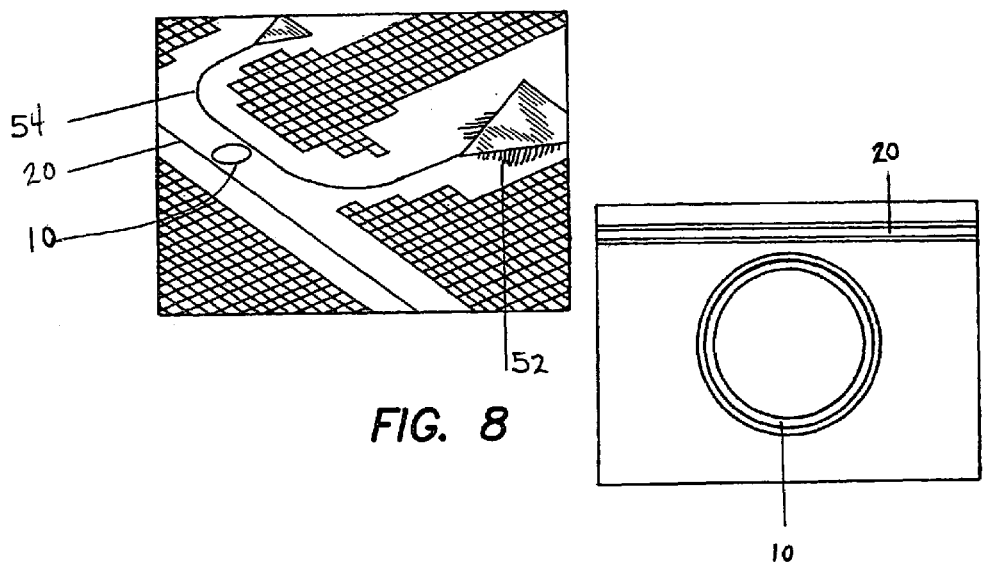
FIG. 8 is a microphotograph showing a nanoresonator filter coupled to a waveguide and to a grating through a drop waveguide.

FIG. 8 shows the geometry for one resonator 10 connected to a grating coupler 52. One grating 52 is used for coupling with a source of laser light, such as a bump bonded semiconductor laser or fiber optic coupled to an off-chip laser light source, and the other detector is coupled to an on-chip detector. The method for measuring many resonators 10 in series comprises the steps in combination of using an input spectrum with many wavelength channels, and under-coupling the resonators 10 to the input waveguides 20'. The optical cavities have to be fabricated to resonate at the peaks in that input spectrum, possible only by the excellent uniformity of deep-UV CMOS lithography with critical dimension control of about 5 nm. Highly sensitive measurements of the surface refractive index and absorption changes can be conducted on a large number of microcavities connected to parallel waveguides 20 by on-chip beamsplitters or gratings 52.

An optical power coupling between fiber-optic waveguides 20 and chip based high Q silicon resonators 10 can be extremely efficient. Coupling efficiencies in excess of 60% have been achieved between optical fiber modes and whispering gallery mode resonances in 5 micron diameter resonators 10. This is all the more remarkable when one considers that the loaded Q's for such small resonators 10 exceed 20,000. FIG. 8 shows a bi-directional resonant coupling configuration in which optical power is resonantly transferred from one waveguide 20 to a second waveguide 54 by coupling through a silicon resonator 10. The high efficiency of this system results from the ideal nature of the four-port waveguide-to-resonator coupling (i.e., negligible parasitic loss) combined with near critical coupling of ring modes by the waveguide 20.

Introduction of minute amounts of loss into the whispering gallery will disturb the critical coupling condition and cause large swings in the resonant coupled power of ring resonator systems. For example, in the above system of FIG. 8, an added optical loss of only 0.05% per round trip is sufficient to create nearly a 100% swing in resonant optical transmission. As such the microring resonator system of FIG. 8 can be configured as a sensor of any mechanism that will absorb or scatter radiation from the whispering gallery.

b. Grating Couplers

The advantage of using SOI wafers for fabricating sensor arrays 12 lies in the ability to leverage the vast infrastructure of the Si microelectronics industry. CMOS processing can routinely obtain very smooth and high Q resonant cavities using thin Si layers. Silicon also offers the possibility of combining optical waveguiding with Ge detectors 18 and high-speed amplification electronics 14. Thus, the use of SOI wafers, which are commercially available in 8" diameters, enable rapid commercialization once an optoelectronic circuit has been optimized. Moreover, the high refractive index contrast between silicon and its oxide permits dramatic miniaturization of optical elements to sizes similar to electronic circuit elements.

However, in order to take advantage of this high refractive index contrast in the Si/SiO$_2$ materials system, new methods for efficiently coupling light into and out of the thin silicon waveguides have to be developed. The mismatch between a single mode optical fiber with a 6000 nm core and a single mode silicon waveguide with a 300 nm vertical and lateral dimension has in the past resulted in enormous insertion losses and prevented the successful application of high-index chip-based waveguide systems.

Figure 9:
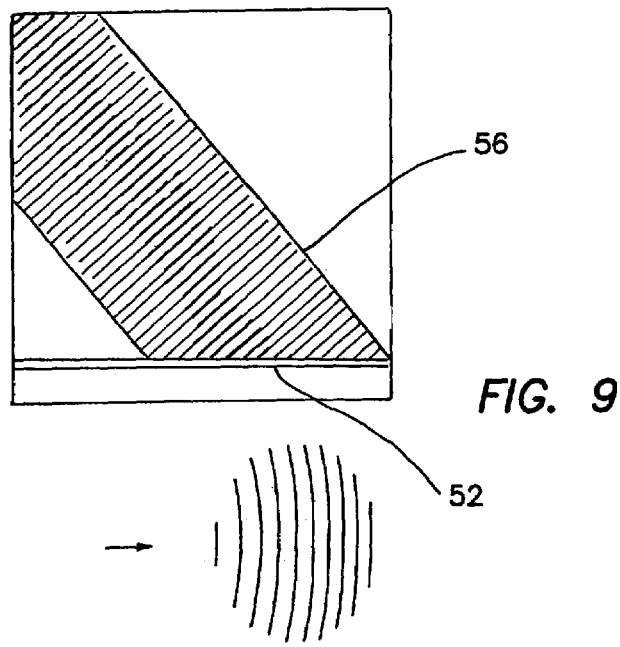
FIG. 9 is a computer two-dimensional simulation of the optical pattern in a coupling between an input fiber and a grating.

Very successful strategies have been developed for coupling light into silicon slabs with low losses over wide spectral windows. FIG. 9 shows a schematic illustration of the approach which we have used for such low-loss coupling. The core of an input fiber 56, shown in the top portion of FIG. 9 at a 45 degree angle, is used to touch a grating 54, which has been defined within a silicon-on-insulator waveguide slab during the CMOS process. Such structures have coupling losses below 2 dB. FIG. 9 shows a side view in the upper portion in which the light wavefronts in the fiber optic are matched to the grating periodicity shown as a horizontal line with ridges connected to the 45 degree angled optic fiber. The lower portion of FIG. 9 is a plan view of the illustration shown in the upper portion of FIG. 9.

The free spectral range of the resonator 10 is inversely proportional to the circumference, i.e., the radius of the resonator 10. Thus, as the resonator diameter increases, the frequency range within which the resonator 10 can be used to add or drop specific frequencies is reduced. Finally, the response time of the resonator 10 is also related to its size. Together with the obvious advantages in miniaturization to increase the density of filters, the combination of all of these factors motivates us to decrease the diameter of the resonator structures.

c. Germanium Detectors

Silicon on insulator (SOI) structures, which have been developed for microelectronic uses, is the starting material for photonic integrated circuits. The Si/SiO$_2$ materials system, which offers ease of fabrication available from silicon processing technology, as well as excellent transparency as a waveguiding material and a high dielectric constant, is particularly useful if optical and electronic functions are to be combined. Of course, single crystal silicon waveguides are not suitable for efficient detection of light, and must be modified in order to allow an optical-to-electronic conversion. When polycrystalline germanium is deposited onto silicon waveguide membranes, it is possible to construct ultra-small and very sensitive p-n diode detectors 18 with low leakage currents and high conversion efficiency. The p-doped polycrystalline germanium is used to generate carriers, and the silicon SOI active layer is used to waveguide the light and to provide a n-type contact to the reverse-biased junction. Such polycrystalline germanium detectors 18, which can serve in demultiplexers for optical telecommunications systems, exhibit low leakage currents and relatively good quantum efficiency. Simple processing, available for both Si and Ge through the use of previously optimized Freon dry etch chemistries, readily enable integration of germanium nanophotonic detectors 18 with silicon slab waveguides 20 by a post-CMOS fabrication step without compromising the high speed of silicon electronic CMOS amplification circuitry 14. The detectors 18 can be spectrally filtered and their response can be accurately tuned either thermally or by optical bleaching. Detectors 18 can be electrically contacted and directly connected to fast and sensitive electronic amplification and signal processing circuitry, leveraging the complexity available in modern CMOS microprocessor technology.

d. Light Sources

The monolithic integration of the microelectronic driving circuitry directly with high quality optical devices is described above. A missing component of the described optical system, which has so far been very difficult to integrate monolithically on silicon, is an efficient light source. Since silicon does not have a direct bandgap, efficient emission of light from this materials system has been elusive. The illustrated embodiment uses an external source to provide the required optical power. The external light source is in principle the optical equivalent of a "d-c power supply" used microelectronic circuits, in which information is multiplexed by the filter resonators 10 on the silicon chip. By taking advantage of our efficient grating couplers, there is little penalty for coupling light from an external pig-tailed CW light source onto the silicon chip. The light source may also be comprised of a filtered tungsten filament lamp, a filtered broad-band light emitting diode, or an inexpensive Fabry-Perot cleaved cavity lasers. Alternatively, a loop of erbium doped fiber can be used as a frequency splitter to generate a predefined fine comb of CW wavelengths, and the precise wavelengths can be selected with an appropriate passive filter on the silicon chip. Pigtailing to optical fiber can be avoided if a vertical cavity surface emitting (VeSEL), or a grating coupled surface emitting laser can be directly bump-bonded onto the silicon chip. Such laser sources are relatively inexpensive if purchased in large numbers. Light sources compatible with the relatively slow sensor applications need to satisfy much less demanding performances than wavelength division multiplexing WDM systems require. Thus it is possible to create a fully functional chemical sensor system with low power dissipation and less expensive sources, enabling operation over long times, background subtraction and lower cost. Such laser sources can be bump bonded or fiber coupled into optical elements fabricated in the substrate or chip.

e. Optical Performance

Figure 10:
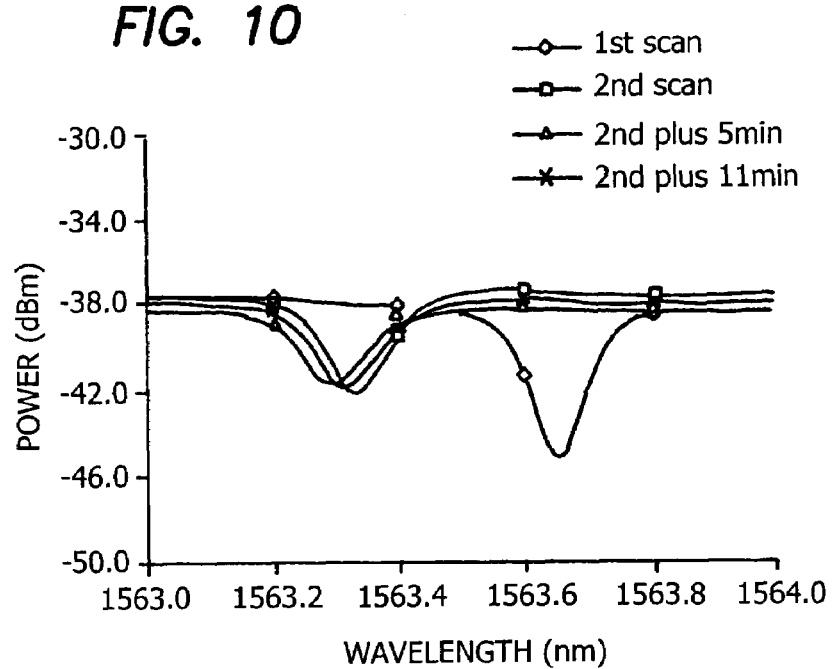
FIG. 10 is a graph of the power as a function of the wavelength spectrum in a silicon waveguide coupled to a ring resonator.

To demonstrate the sensitivity of the proposed optically interrogated sensors 22, silicon ring resonators 10 are coated with polymers 16 that are sensitive to oxygen. The results are summarized in FIG. 10, where the wavelength spectrum of a silicon waveguide 20 coupled to a ring resonator 10 is shown. FIG. 10 shows four graphs of power verses wavelength for a ring resonator. The minimum dip shown to the right is the frequency response of the ring resonator without any analyte reaction, in this example with oxygen. The minimums to the left are three nearly overlapping dips which occur after the ring resonator was exposed to the functionalized molecule, oxygen, after 5 minutes and then 11 minutes of exposure. The minimum moves very slightly to the left in the graph as a function of time or completion of reaction. In this geometry, the ring resonator 10 acts as a drop filter for the wavelength resonant in the ring cavity, and the Q of the resonator can be used to deduce the optical bend and absorption losses. Initially, the resonator quality of a polymer-coated resonator, shown in blue to resonate at 1563.6 nm, is calculated at 16,800. As the polymer-coated resonator 10 is exposed to oxygen and the refractive index of the polymer changes, the resonator channel drop frequency is reduced by 0.2 nm to a value of 1543.3 nm, corresponding to an equivalent refractive index change in the polymer of 0.3%. At the same time, the Q of the resonator 10 deteriorates from 16,800 to 7,000 after 11 minutes of oxygen exposure. Ultimately, this data shows that, for a resonator cavity with a Q of about 20,000, a refractive index sensitivity of 0.01% can be achieved.

Figure 11:
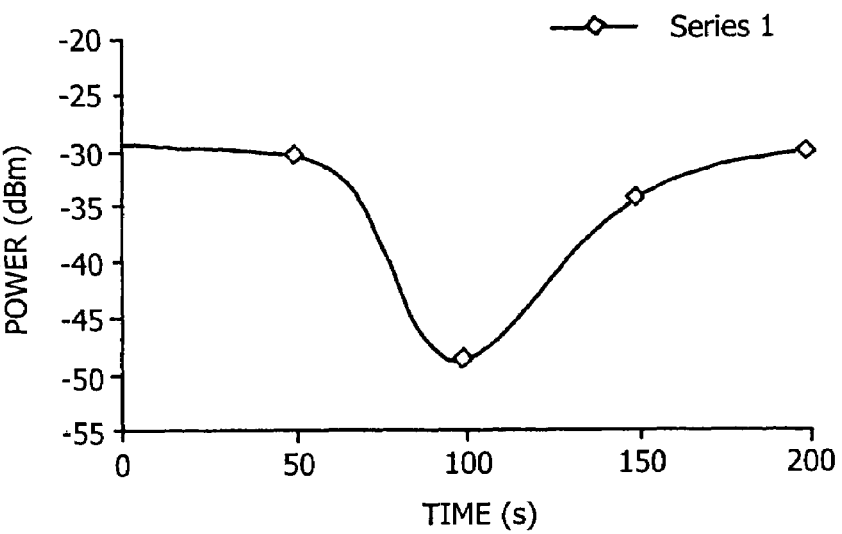
FIG. 11 is a graph of power as a function of time, which shows such a time-dependent response curve for a resonator with a 2000 nm thick polymer layer, and shows a response time of several seconds.

One of the advantages of the illustrated sensor geometry lies in the opportunity of using very thin polymer layers 16 to coat the resonator cavities 10. By using thin sensor layers 16, the detection speed, which is generally diffusion limited, can be increased significantly, especially when measuring very dilute gas mixtures. To illustrate the time sensitivity of a polymer layer 16, the time-dependent optical signal is measured at a fixed frequency as the resonance peak is tuned by the chemical reaction past the measured wavelength. FIG. 11 is a graph of power verses time which shows such a time-dependent response curve for a 2000 nm thick polymer layer 16, and shows a response time of several seconds. FIG. 11 is a graph of power verses time for a ring resonator at a fixed frequency, which shows that a response is seen prior to saturation which occurs later at a different frequency. As the thickness of polymer is reduced to the 500 nm which are needed for optimum refractive index response, this response time can be further improved to below 1 second.

An ideal chemical analysis system is comprised of inexpensive and disposable components, and contain a very compact, robust and intelligent measurement system. The optical read-out chips are a generic platform for a large number of different chemical analysis functions, since the read-out mechanism is based entirely on modified CMOS electronics and optics, and their functionality is determined by the large array of chemical sensing polymers which are retroactively deposited onto the filtered detector array in a post-processing step. The sensor array 12 is very sensitive due to the enormous path length of interaction between light and the sensor polymer 16, and on-chip readout electronics 14 provide diagnostic information on the condition of the sensor performance and electronic intelligence or signal analysis in the read-out process. Performance of the resonators varies with time, temperature, frequency and other environmental or manufacturing parameters which will need to be deconvolved according to the physics of the experiment to obtain a true or reliable detection signal. This can be accomplished with conventional signal analysis circuitry implemented in CMOS circuitry fabricated with the ring resonators on chip. With the addition of appropriate information processing electronics, an integrated optical sensor system created on a SOI substrate, the choice platform for high speed low-power microprocessor chips, provides accurate analysis results on thousands of chemicals in parallel. This unusual ability is coupled with the flexibility of integrating soft lithography for chemical concentration and delivery, and shows much promise as a very flexible read-out system for the definition of a spectroscopic laboratory on a chip. In such a system, a wide variety of either air-borne or fluidic chemical agents can be quantitatively measured with high certainty and required redundancy. Here, a geometry was described which lends itself to massive integration due to the small footprint of the optical sensor elements 22, and which satisfies the requirements of an integrated measurement system, in which sensitive and intelligent analysis of data from thousands of sensors 22 can be undertaken. A very large number of sensors 22 may be randomly addressed within a single array 12 by applying addressing techniques typically found in CMOS memory circuits as illustrated in FIG. 12a.

This approach, when used with optimized sensor arrays and appropriate electronic logic, offers equivalent performance to commercially available spectrophotometers in a much smaller volume, and enables integration with mobile platforms where volume, energy consumption and robustness are at a premium. Moreover, the 0.13 micron CMOS fabrication technology used in the construction of the chemical sensors 22 can be used to build a wireless interface directly onto the sensor chip 12, which then could Le used for transmitting sensor data in military applications where a distributed array of remote sensors need to be deployed to communicate through a simple wireless network.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A microsensor for sensing a substance comprising:
a substrate;
a source of light;
an optical microresonator fabricated in the substrate exposed to the substance to allow an interaction between the microresonator and substance;
a waveguide coupling the source of light to the optical microresonator; and
a detector coupled to the microresonator to measure a performance parameter of the optical microresonator sensitive to interaction of the substance with the optical microresonator,
where the performance parameter is the absorption loss of whispering gallery modes in the microresonator.

2. A microsensor for sensing a substance comprising:
a substrate;
a source of light;
an optical microresonator fabricated in the substrate exposed to the substance to allow an interaction between the microresonator and substance;
a waveguide coupling the source of light to the optical microresonator; and
a detector coupled to the microresonator to measure a performance parameter of the optical microresonator sensitive to interaction of the substance with the optical microresonator,
where the waveguide comprises a CMOS fabricated waveguide and the detector is comprises a detector deposited onto the CMOS fabricated waveguide.

3. A microsensor for sensing a substance comprising:
a substrate;
a source of light;
an optical microresonator fabricated in the substrate exposed to the substance to allow an interaction between the microresonator and substance;
a waveguide coupling the source of light to the optical microresonator; and
a detector coupled to the microresonator to measure a performance parameter of the optical microresonator sensitive to interaction of the substance with the optical microresonator,
where the microresonator is characterized by an optical absorption loss determined by direct optical excitation of the substance when in contact with the microresonator.

4. The microsensor of claim 3 further comprising a plurality of microresonators corresponding to a plurality of different resonant frequencies to generate an absorption spectrum of the substance.

5. A microsensor for sensing a substance comprising:
a substrate;
a source of light;
an optical microresonator fabricated in the substrate exposed to the substance to allow an interaction between the microresonator and substance;
a waveguide coupling the source of light to the optical microresonator;
a detector coupled to the microresonator to measure a performance parameter of the optical microresonator sensitive to interaction of the substance with the optical microresonator; and
a plurality of microsensors organized in an addressable array on the substrate, ones of the plurality of microsensors being resonant at or tuned to different optical frequencies, absorption losses of the plurality of microsensors being measured as a result of optical coupling between an analyte and ones of the resonators as determined by the resonant frequency of the microresonator and the absorption peak of the analyte, whereby an absorption spectrum of direct spectroscopy of an analyte or absorption of antibody-linked fluorescent molecules used as markers are measured.

6. A microsensor for sensing a substance comprising:

a substrate;

a source of light;

an optical microresonator fabricated in the substrate exposed to the substance to allow an interaction between the microresonator and substance;

a waveguide coupling the source of light to the optical microresonator;

a detector coupled to the microresonator to measure a performance parameter of the optical microresonator sensitive to interaction of the substance with the optical microresonator;

a plurality of microresonators and a corresponding plurality of detectors formed into an array coupled by the waveguide to the light source in which the plurality of microresonators are exposed to a plurality of substances;

an addressing circuit for reading the array; and a CMOS integrated read-out circuitry fabricated in the substrate coupled to the addressing circuit, where the CMOS integrated read-out circuitry provides diagnostic information on the condition of sensor performance and electronic intelligence in a read-out process.

7. The microsensor of claim 6 further comprising a wireless interface fabricated on the substrate and communicated to the read-out circuitry.

8. A method for sensing a substance comprising:

providing a substrate;

providing a source of light;

communicating the light through a waveguide coupled to the source of light to an optical microresonator fabricated in the substrate exposed to the substance to allow an interaction between the microresonator and substance; and detecting the interaction between the microresonator and substance by measurement of a performance parameter of the optical microresonator, where detecting the interaction between the microresonator and substance comprising detecting, the optical performance of a semiconductor optical ring microresonator;

where detecting the optical performance of a semiconductor optical ring microresonator comprises measuring the optical performance of a microresonator with an initial Q of 10,000 or greater, where measuring the optical performance of a microresonator comprises measuring the absorption loss of whispering gallery modes in the microresonator.

9. A method for sensing a substance comprising:

providing a substrate;

providing a source of light;

communicating the light through a waveguide coupled to the source of light to an optical microresonator fabricated in the substrate exposed to the substance to allow an interaction between the microresonator and substance;

detecting the interaction between the microresonator and substance by measurement of a performance parameter of the optical microresonator; and providing a plurality of microsensors organized in an addressable array on the substrate, ones of the plurality of microsensors being resonant at or tuned to different optical frequencies, measuring the absorption losses of the plurality of microsensors as a result of optical coupling between an analyte and ones of the resonators as determined by the resonant frequency of the microresonator and the absorption peak of the analyte, and generating an absorption spectrum of direct spectroscopy of an analyte or absorption of antibody-linked fluorescent molecules used as markers are measured.

10. A method for sensing a substance comprising:

providing a substrate;

providing a source of light;

communicating the light through a waveguide coupled to the source of light to an optical microresonator fabricated in the substrate exposed to the substance to allow an interaction between the microresonator and substance; and detecting the interaction between the microresonator and substance by measurement of a performance parameter of the optical microresonator;

providing a plurality of microresonators and a corresponding plurality of detectors configured into an array coupled by the waveguide to the light source and exposing the plurality of microresonators to the substance or plurality of substances;

fabricating an addressing circuit on the substrate for reading the array;

fabricating CMOS integrated read-out circuitry in the substrate coupled to the addressing circuit; and generating diagnostic information on the condition of sensor performance and electronic intelligence by means of the integrated read-out circuitry.

11. A method for sensing a substance comprising:

providing a substrate;

providing a source of light;

communicating the light through a waveguide coupled to the source of light to an optical microresonator fabricated in the substrate exposed to the substance to allow an interaction between the microresonator and substance; and detecting the interaction between the microresonator and substance by measurement of a performance parameter of the optical microresonator;

providing a plurality of microresonators and a corresponding plurality of detectors configured into an array coupled by the waveguide to the light source and exposing the plurality of microresonators to the substance or plurality of substances;

fabricating an addressing circuit on the substrate for reading the array;

fabricating CMOS integrated read-out circuitry in the substrate coupled to the addressing circuit; and fabricating a wireless interface on the substrate communicated to the read-out circuitry.

* * * * *